United States Patent [19]

Galluzzo

[11] Patent Number: 4,869,242

[45] Date of Patent: Sep. 26, 1989

[54] BONE FIXATION PIN AND METHOD OF USING THE SAME

[76] Inventor: Mose A. Galluzzo, 3106 N. Rockton Ave., Rockford, Ill. 61103

[21] Appl. No.: 225,773

[22] Filed: Jul. 29, 1988

[51] Int. Cl.⁴ .......................... A61F 5/04; F16B 15/00; F16B 15/02

[52] U.S. Cl. .......................... 128/92 ZW; 128/92 YE; 411/474; 411/476; 411/482

[58] Field of Search .......... 128/92 Z, 92 ZW, 92 YK, 128/92 YV, 92 YT, 92 YE, 92 VS, 92 YW; 411/474, 476, 473, 482, 485

[56] References Cited

U.S. PATENT DOCUMENTS

| | | | |
|---|---|---|---|
| 1,561,518 | 11/1925 | Graham | 411/474 |
| 1,765,729 | 6/1930 | LaMorte | 411/482 |
| 1,792,217 | 2/1931 | Farr | 411/482 |
| 2,034,573 | 3/1936 | Goehring | 411/482 |
| 2,114,451 | 4/1938 | Mattes | 411/482 |
| 2,570,465 | 10/1951 | Lundholm | 128/92 YV |
| 2,874,603 | 2/1959 | Boettcher | 411/482 |
| 3,205,757 | 9/1965 | Kuennen | 411/473 |
| 3,842,824 | 10/1974 | Neufeld | 128/92 YV |
| 3,915,162 | 10/1975 | Miller | 128/92 YE |
| 3,915,166 | 10/1975 | McCrink | 128/866 |
| 4,138,921 | 2/1979 | McGauran | 411/476 |

Primary Examiner—Robert A. Hafer
Assistant Examiner—Michael Brown
Attorney, Agent, or Firm—Leydig, Voit & Mayer

[57] ABSTRACT

A bone fixation pin includes an elongated pointed shank having an enlarged head at one end thereof. A second shank projects axially from the other end of the head and is joined to a second head which, in turn, is integral with a third shank. An enlarged and relatively long head on the end of the third shank may be gripped by the rotary chuck of a tool for driving the pin. After the pin has been driven into the bone of a digit, the exposed end portion of the pin is detached from the pin by snapping the pin either at the relatively weak second shank or at the relatively weak third shank. A flexible tie for pulling two parallel pins toward one another and placing an osteotomy site in compression may be looped around each pin and captivated axially by the first and second heads.

8 Claims, 1 Drawing Sheet

BONE FIXATION PIN AND METHOD OF USING THE SAME

BACKGROUND OF THE INVENTION

This invention relates to bone fixation and, more particularly, to the pinning of the bone of a digit such as a toe following an injury thereto or surgery thereon.

Presently existing bone fixation pins comprise an elongated piece of stainless steel having a point on one end. The pin is adapted to be driven into the digit in the area of an injury or osteotomy. A tool similar to a wire cutter then is used to cut off excess length from the exposed outer end portion of the pin.

SUMMARY OF THE INVENTION

The general aim of the present invention is to provide a new and improved bone fixation pin which lends itself to quick, easy and simple application.

Another object of the invention is to provide a unique fixation pin adapted to coact with a flexible tie and with a second fixation pin to place the bone at an osteotomy site in compression and to maintain such compression during healing.

In a more detailed sense, the invention resides in the provision of a novel bone fixation pin having a shank with a pointed end, a head on the opposite end portion of the shank, a second shank extending from the head, and a second head on the free end of the second shank.

These and other objects and advantages of the invention will become more apparent from the following detailed description when taken in conjunction with the accompanying drawings.

DETAILED DESCRIPTION OF THE PREFERRED EMBODIMENT

Figure 1:
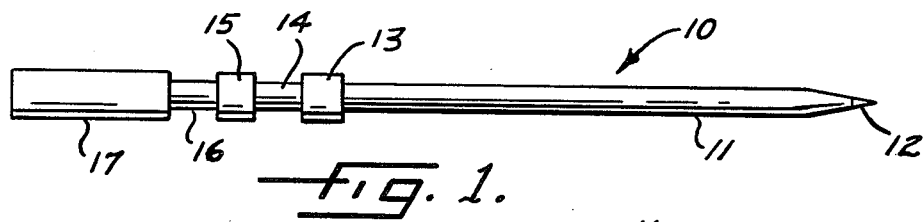
FIG. 1 is a side elevational view of a new and improved bone fixation pin incorporating the unique features of the present invention.

A bone fixation pin 10 of the present invention is shown most clearly in FIG. 1. It is formed by a single piece of stainless steel or other appropriate material.

More specifically, the pin 10 includes an elongated cylindrical shank 11 which, in this particular instance, has a length of about 1¼" and a diameter of about 0.050". The free end of the shank has a point 12 which is formed by beveling diametrically opposite sides of the pin at an angle of about 10 degrees.

Formed integrally with the shank 11 on the end thereof opposite the point 12 is an enlarged cylindrical head 13. The head has a length of about 0.090" and a diameter of about 0.093".

Pursuant to the invention, a second shank 14 is formed integrally with the head 13 and projects axially therefrom in a direction opposite to the direction of projection of the shank 11. The shank 14 is cylindrical and has the same diameter as the shank 11 but is significantly shorter, the shank 14 herein having a length of about 0.100".

Figures 2, 3:
FIG. 2 is a bottom plan view of the pointed end portion of the pin.
FIG. 3 is an end view of the pin as viewed from the right of FIG. 2.

A second head 15 which preferably is identical in size and shape to the head 13 is located at the outer end of the shank 14 while a third shank 16 which is identical in size and shape to the shank 14 projects outwardly from the head 15. The pin is completed by a third cylindrical head 17 having a diameter of 0.093" and a length of about 0.40". The longer length of the head 17 enables the head to be securely gripped by a rotatable chuck 18 (FIG. 2) which forms the nose of a tool for driving the pin 10.

Figure 4:
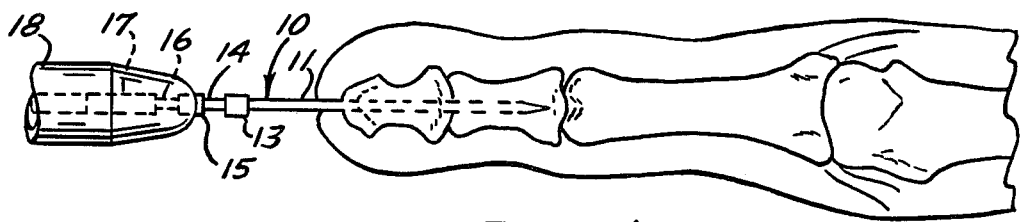
FIG. 4 is a view showing the pin being driven axially into the end of a digit.
Figure 5:
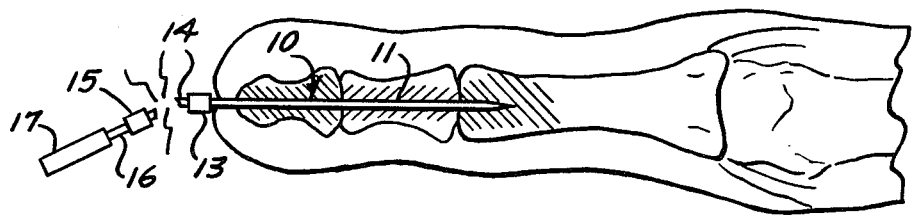
FIG. 5 is a view similar to FIG. 4 but shows the pin fully driven and the exposed end portion thereof being broken away.

FIG. 4 shows the pin 10 as it is being driven axially into a toe from the distal end of the toe and along the length thereof. After the pin has been driven to an appropriate depth, substantially all of the exposed end thereof is broken away by holding the toe rigid and by moving the chuck in such a manner as to snap the exposed portion of the pin away from the remainder of the pin along a fracture line located in a generally radial plane. When the pin is positioned as shown in FIG. 4, snapping of the pin occurs at the reduced-diameter and relatively weak shank 14. In this condition, the head 13 is just outside of the distal end of the toe.

Figure 6:
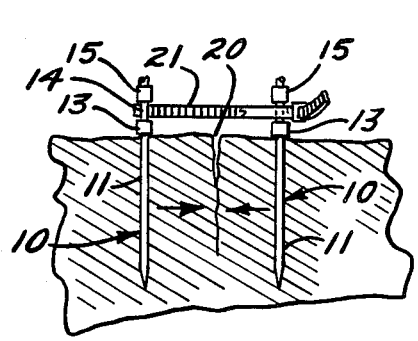
FIG. 6 is a cross-sectional view through the bone of a digit and shows the osteotomy site being held in compression by two of the fixation pins and a flexible tie.

Two of the pins 10 may be used to advantage to place the bone at an osteotomy site 20 (FIG. 6) in compression and to hold the osteotomy site in compression during healing. FIG. 6 shows such use of the pins and, as illustrated, the pins are driven into the bone on opposite sides of the osteotomy site and are located in spaced parallel relation with the inner ends of the heads 13 adjacent the bone. After the pins have been so located, each pin is snapped off at the shank 16 so as to enable the driving head 17 to be removed and discarded.

Following driving of the two pins 10, a flexible tie 21 is looped around the pins and is cinched so as to pull the outer ends of the pins toward one another and thereby place the osteotomy site in compression. Advantageously, the tie is formed by an elongated strip of plastic having a height just slightly less than the spacing between the heads 13 and 15 of each pin. Thus, the heads 13 and 15 captivate the tie axially on the pin.

Figure 7:
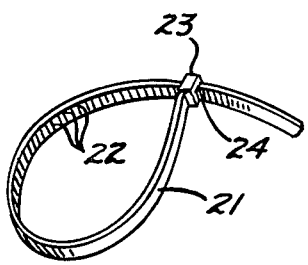
FIG. 7 is a perspective view of the flexible tie shown in FIG. 6.

While various forms of ties may be used, the preferred tie 21 is formed with a series of spaced detents or lugs 22 (FIG. 7) along the major portion of its length. One end of the tie is defined by an eye 23 having detent means 24 which enable the strip to move freely through the eye when the strip is drawn through the eye in one direction. Thus, the tie may be placed in tension and cinched around the pins 10 to pull the outer ends of the pins toward one another and compress the osteotomy site 20. After an appropriate degree of tension has been placed in the tie, the detent means 24 is locked releasably against one of the lugs 22 so as to maintain the holding force.

From the foregoing, it will be apparent that the present invention brings to the art a new and improved bone fixation pin 10 which may be applied quickly and easily by virtue of driving the pin with the chuck 18 and by using the chuck to break off the end of the pin. Moreover, the use of two pins in combination with the tie 21 enables an osteotomy site to be placed and securely held in compression.

I claim:

1. The combination of, a pair of bone fixation pins adapted to be driven into a bone in spaced and substantially parallel relation on opposite sides of an osteotomy site, and a tie for pulling said pins toward one another to hold the joint at the osteotomy site in compression, each of said pins comprising:
    (a) a first elongated and generally cylindrical shank having a point on one end thereof;
    (b) a first enlarged diameter head integral with the opposite end of said shank;
    (c) a second shank of smaller diameter than said head and integral with said head, said second shank projecting axially from said head in a direction opposite to the direction of projection of said first shank and being substantially shorter than said first shank, and
    (d) a second enlarged diameter head integral with said second shank and spaced axially from said first head;

said tie comprising an elongated flexible member having a width less than the axial spacing between the first and second heads of each pin whereby said flexible member may be looped around the second shank of each pin and captivated axially by the heads thereof, and means for cinching the end portions of said flexible member together and for holding such end portions in cinched relation whereby said flexible member forces the second shank of each pin toward the second shank of the other pin.

2. The combination defined in claim 1 in which said means comprise a plurality of spaced detents on one end portion of said flexible member, and an eye on the other end of said flexible member and adapted to receive said one end portion, said eye having means permitting said one end portion of said flexible member to be drawn through said eye in one direction while releasably holding said one end portion against movement within said eye in the opposite direction.

3. The combination defined in claim 1 in which each pin further includes:
    (e) a third shank of smaller diameter than said second head and integral with said second head, said third shank projecting axially from said second head in a direction opposite to the direction of projection of said second shank and being substantially shorter than said first shank, and a third enlarged diameter head integral with said third shank and spaced axially from said second head.

4. The combination defined in claim 3 in which the axial length of said second head of each pin is approximately equal to the axial length of the first head thereof, the axial length of said third head being substantially greater than the axial length of said second head.

5. The combination defined in claim 1 in which each pin further includes a driver element spaced axially from said second head, and means integral with and located between said second head and said driver element and defining a weakened area enabling said driver element to be broken away from said second head.

6. A bone fixation pin comprising a first elongated cylindrical shank of predetermined diameter and having a point on one end thereof, said shank being adapted for driving into a human bone, a first head integral with the opposite end of said shank and having a diameter greater than the diameter of the shank, a second shank integral with said head and having a diameter smaller than the diameter of said head, said second shank projecting axially from said head in a direction opposite to the direction of projection of said first shank and being substantially shorter than said first shank, a second head integral with said second shank and having a diameter larger than the diameter of said second shank, said second head being spaced axially from said first head whereby an annular groove is defined between said heads, a driver head spaced axially from said second head, and means integral with and located between said second head and said driver head and defining a weakened area enabling said driver head to be broken away from said second head.

7. A method of using two bone fixation pins and an elongated flexible tie to place and retain in compression an osteotomy site of the bone of a digit, each of said pins comprising:
    (a) a first elongated and generally cylindrical shank having a point on one end thereof;
    (b) a first enlarged diameter head integral with the opposite end of said shank;
    (c) a second shank of smaller diameter than said head and integral with said head, said second shank projecting axially from said head in a direction opposite to the direction of projection of said first shank and being substantially shorter than said first shank, and
    (d) a second enlarged diameter head integral with said second shank and spaced axially from said first head;

said method comprising the steps of, driving said pins point first and generally radially of said digit in locations to place said pins in generally spaced parallel relation on opposite sides of said osteotomy site, looping said tie around the second shank of each pin between the first and second heads thereof, and cinching the end portions of said tie together while the tie is under tension thereby to cause the tie to pull the second shanks of said pins toward one another.

8. A method as defined in claim 7 in which each of said pins comprises a driver element spaced axially from said second head, means integral with and located between the second head and the driver element of each pin and defining a weakened area enabling the driver element to be broken away from the second head, said method further comprising the step of breaking the driver element of each pin away from the second head thereof after the pin has been driven into said digit.

* * * * *